United States Patent [19]

Pollock

[11] Patent Number: 5,185,153
[45] Date of Patent: Feb. 9, 1993

[54] AGENTS EFFECTING THE LYSIS OF ORAL BACTERIA

[75] Inventor: Jerry J. Pollock, Nesconset, N.Y.

[73] Assignee: The Research Foundation of the State University of New York, Albany, N.Y.

[21] Appl. No.: 592,552

[22] Filed: Oct. 4, 1990

[51] Int. Cl.$^5$ .............................................. A61K 9/28
[52] U.S. Cl. ...................................... 424/440; 424/49
[58] Field of Search ................................... 424/440, 49

[56] References Cited

U.S. PATENT DOCUMENTS

| | | | |
|---|---|---|---|
| 2,689,170 | 9/1954 | King | 424/54 |
| 3,257,450 | 6/1966 | Globus | 260/505 |
| 3,342,687 | 9/1967 | Gould | 167/93 |
| 4,032,663 | 6/1977 | Kobayashi et al. | 426/51 |
| 4,067,962 | 1/1978 | Juneja | 424/52 |
| 4,150,151 | 4/1989 | Pader et al. | 424/56 |
| 4,156,716 | 5/1979 | Wagenknecht et al. | 424/48 |
| 4,161,517 | 7/1979 | Wagenknecht et al. | 424/48 |
| 4,178,362 | 12/1979 | Hoogendoorn et al. | 424/48 |
| 4,198,392 | 4/1980 | Juneja | 424/48 |
| 4,409,202 | 10/1988 | Witzel | 424/49 |
| 4,525,343 | 6/1985 | Raaf | 424/54 |
| 4,585,649 | 4/1986 | Lynch | 424/49 |
| 4,618,489 | 10/1986 | Pollock et al. | 424/52 |
| 4,657,758 | 4/1987 | Goldemberg et al. | 424/49 |
| 4,666,708 | 5/1987 | Goldemberg et al. | 424/49 |
| 4,824,661 | 4/1989 | Wagner | 424/52 |
| 4,837,008 | 6/1989 | Rudy et al. | 424/53 |
| 4,844,883 | 7/1989 | Patel | 424/49 |
| 4,846,650 | 7/1989 | Benedict et al. | 424/55 |
| 4,861,582 | 8/1989 | Pollock | 424/520 |
| 4,950,479 | 8/1990 | Hill | 424/49 |

FOREIGN PATENT DOCUMENTS

| | | |
|---|---|---|
| 29332A1 | 5/1981 | European Pat. Off. . |
| 1504207 | 10/1967 | France . |
| 376604 | 7/1932 | United Kingdom . |

OTHER PUBLICATIONS

Pollock et al., *Journal of Dental Research*, 66, 467–474 (1987).
Pollock et al., *Infection and Immunity*, 45, 610–617 (1984).
Polson and Caton, *Journal of Periodontology, Supplement*, 56, 1–3 (1985).
Flemmig et al., *Journal of Dental Research, Abstracts*, 68, Abstract #1612 (1989).

*Primary Examiner*—Thurman K. Page
*Assistant Examiner*—D. Gabrielle Phelan
*Attorney, Agent, or Firm*—Hoffmann & Baron

[57] ABSTRACT

The present invention provides compositions for the lysis and killing of microbes in general, and in particular provides oral compositions for the lysis and killing oral bacteria. The compositions of the present invention include a humectant such as glycerol, sorbitol or comparable compounds and provide an in-mouth concentration of such substances from about 20% to about 80% weight/volume in dentifrice preparations, in particular mouthrinses. These compositions further comprises (a) bicarbonate ion at about 0.5% to about 2% wt./vol. and if desired, thiocyanate, chloride or fluoride ion at about 0.5% to about 2% wt./vol. (b) sodium lauroyl sarcosinate or other anionic detergents from about 0.05% to about 1% wt./vol. and (c) Tween 20 or other non-ionic detergents or structurally similar compounds from about 0.01% to about 3% vol./vol. In addition, alcohol may be added up to a level of 15% vol./vol. along with appropriate sweetening and flavoring agents. Water is then added to 100%. The compositions may be introduced in a manner and vehicle suitable for oral cavity administration. This invention also relates to a method of using such compositions for treating and inhibiting dental caries, dental plaque and gingivitis, oral malodor and periodontopathic conditions in mammals, particularly humans, in need of anti-caries, anti-plaque, anti-gingivitis, anti-malodor or anti-periodontopathic therapy. The compositions of the present invention are conventionally formulated into mouthrinses (mouth washes) and the commonly utilized dentifrice treatment agents.

12 Claims, 8 Drawing Sheets

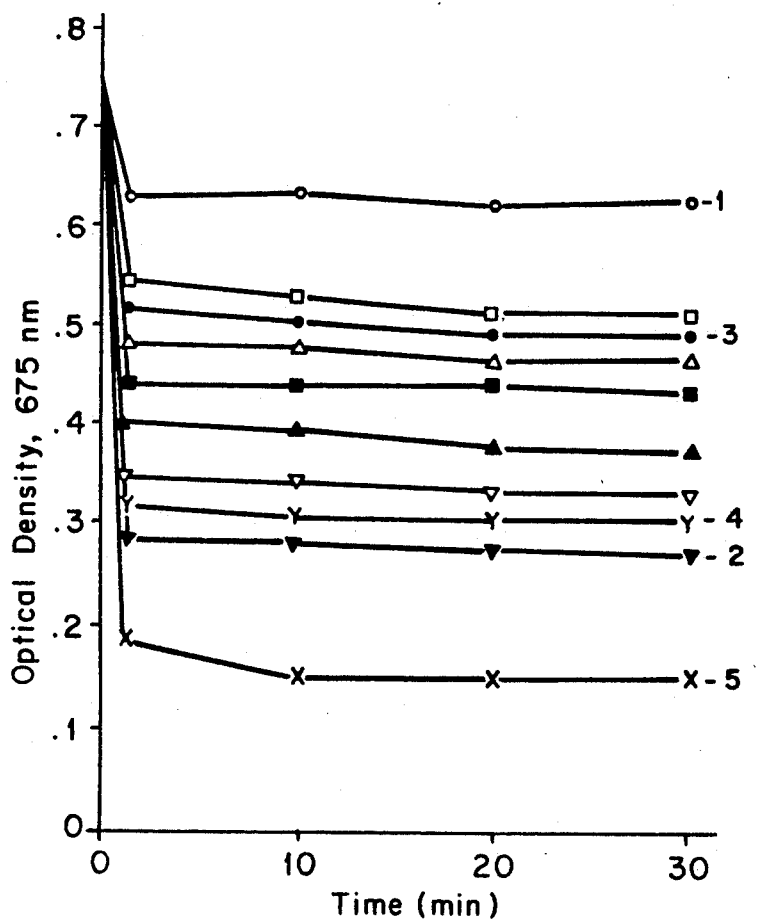

FIG. 1

LEGEND

○ WATER CONTROL
● 1.5% SODIUM BICARBONATE
   + 0.5% SODIUM THIOCYANATE
□ 10% GLYCERIN OR SORBITOL
△ 15% GLYCERIN OR SORBITOL
■ 20% GLYCERIN OR SORBITOL
▲ 25% GLYCERIN OR SORBITOL
▽ 30% GLYCERIN OR SORBITOL
▼ 40% GLYCERIN OR SORBITOL
X   40% GLYCERIN (OR SORBITOL)
     + 3% TWEEN 20 + 7.5% ETHANOL
     + 1.5% SODIUM BICARBONATE
     + 0.5% SODIUM THIOCYANATE
Y   20% GLYCERIN (OR SORBITOL)
     + 3% TWEEN 20 + 7.5% ETHANOL
     + 1.5% SODIUM BICARBONATE
     + 0.5% SODIUM THIOCYANATE

LEGEND

○ WATER CONTROL

● 1.5% SODIUM BICARBONATE + 0.5% SODIUM THIOCYANATE

△ 40% GLYCERIN

□ 40% GLYCERIN + 3% TWEEN 20

♦ 40% GLYCERIN + 3% TWEEN 20 + 7.5% ETHANOL + 1.5 SODIUM BICARBONATE + 0.5 SODIUM THIOCYANATE + 0.5% SODIUM LAUROYL SULFATE

▽ 20% GLYCERIN + 3% TWEEN 20 + 7.5% ETHANOL + 1.5% SODIUM BICARBONATE + 0.5% SODIUM THIOCYANATE + 0.5% SODIUM LAUROYL SULFATE

LEGEND

O  WATER CONTROL

●  0.5% SODIUM LAUROYL SULFATE

X  40% GLYCERIN + 3% TWEEN 20 + 7.5% ETHANOL + 1.5% SODIUM BICARBONATE + 0.5% SODIUM THIOCYANATE

♦  40% GLYCERIN + 3% TWEEN 20 + 7.5% ETHANOL + 1.5% SODIUM BICARBONATE + 0.5% SODIUM THIOCYANATE + 0.5% SODIUM LAUROYL SULFATE

LEGEND

○ WATER CONTROL

● 0.5% SODIUM LAUROYL SULFATE

▽ 40% GLYCERIN + 3% TWEEN 20 + 0.5% SODIUM LAUROYL SULFATE

◆ 40% GLYCERIN + 3% TWEEN 20 + 0.5% SODIUM LAUROYL SULFATE + 7.5% ETHANOL + 1.5% SODIUM BICARBONATE + 0.5% SODIUM THIOCYANATE

LEGEND

○ WATER CONTROL

● 40% GLYCERIN

△ 40% GLYCERIN + 1% TWEEN 20 + 7.5% ETHANOL + 1.5% SODIUM BICARBONATE + 0.5% SODIUM THIOCYANATE + 1% SODIUM LAUROYL SULFATE

□ 40% GLYCERIN + 2% TWEEN 2% + 7.5% ETHANOL + 1.5% SODIUM BICARBONATE + 0.5% SODIUM THIOCYANATE + 1% SODIUM LAUROYL SULFATE

◆ 40% GLYCERIN + 3% TWEEN 20 + 7.5% ETHANOL + 1.5% SODIUM BICARBONATE + 0.5% SODIUM THIOCYANATE + 1% SODIUM LAUROYL SULFATE

▽ PLAX

LEGEND

O  WATER CONTROL

♦  40% GLYCEROL (OR 40% SORBITOL) + 3% TWEEN 20 + 7.5% ETHANOL + 1.5% SODIUM BICARBONATE + 0.5% SODIUM THIOCYANATE + 0.5% SODIUM LAUROYL SULFATE

LEGEND

O  WATER CONTROL

●  2% SODIUM BICARBONATE

◆  40% GLYCEROL (OR SORBITOL) + 3% TWEEN 20 + 7.5% ETHANOL
   + 1.5% SODIUM BICARBONATE + 0.5% SODIUM THIOCYANATE
   + 0.5% SODIUM LAUROYL SULFATE

LEGEND

○  WATER CONTROL

●  2% SODIUM BICARBONATE

◆  40% GLYCEROL (OR SORBITOL) + 3% TWEEN 20 + 7.5% ETHANOL
   + 1.5% SODIUM BICARBONATE + 0.5% SODIUM THIOCYANATE
   + 0.5% SODIUM LAUROYL SULFATE

AGENTS EFFECTING THE LYSIS OF ORAL BACTERIA

BACKGROUND OF THE INVENTION

The present invention relates to antimicrobial oral compositions, particularly dental rinses, dentifrices and the use of these oral compositions for effecting the lysis of oral bacteria.

The removal of dental plaque and the prevention of new plaque build-up are important for the prevention and treatment of gingivitis and periodontal diseases. A successful therapeutic composition for the treatment of oral disease should satisfy the following criteria:

(i) It should rapidly lyse and kill oral bacteria. The contact time for a dentifrice preparation in the mouth is limited to usually no more than a minute.

(ii) It should kill all bacteria forming or embedded within the plaque. If any bacteria forming or embedded within the plaque are resistant to the action of the dentifrice preparation, then these residual bacteria will become the major component of the oral flora and may contribute to oral disease.

(iii) The composition should be readily available, without prescription to allow continuous daily treatment of the oral cavity. The continued availability of the dentifrice preparation is needed since bacteria readily re-establish themselves in the absence of treatment.

Death of bacteria can be achieved either by bacteriocidal action (death without cellular lysis) or by a bacteriolytic action (death with lysis of the cell). In contrast to the bacteriocidal event where damage may be minimal, bacteriolysis leads to extensive cell wall and cell membrane damage followed by rupture of the bacterial cell and the release of cytoplasmic macro-molecular nucleic acid. Agents that can elicit bacteriolysis are superior for the treatment of oral disease, because once lysed, the oral bacteria (which cause the oral disease) and their contents are completely washed off the oral surfaces (teeth, gums, tongue, cheek, etc.), swallowed and ultimately digested in the stomach where they are rendered harmless. In the process, the network of bacteria that resides on the oral surfaces (the dental plaque) is completely disrupted since bacteriolysis results in the damage and loss of cell wall receptors responsible for both generalized interbacterial adherence and specific coaggregation between bacteria. As surface layers of the dental plaque are shed, the deeper layers of the plaque now become accessible to the action of the bacteriolytic agent which results in further reduction of the amount of bacteria in the mouth. When levels of oral bacteria are sufficiently reduced, then the severity of oral diseases, such as dental caries, gingivitis, periodontitis and oral malodor is in turn reduced.

Dental rinse formulations for loosening plaque present on dental surfaces, rendering it more amenable to removal during brushing with conventional dentifrices are described in U.S. Pat. Nos. 4,657,758 and 4,666,708 ("the '758 and '708 patents"). Neither of these patents describes or suggests an oral rinse composition for lysing of oral bacteria. The compositions described in these patents include high levels of sodium benzoate at least about 2%, to impart antiseptic properties, and an anti-bacterial agent such as sodium salicylate, as an oral antiseptic, which functions as an aid to the solubilization and removal of plaque from the dental surface. Other ingredients of the formulations may include benzethenium chloride, N-alkylpyridinium chloride, N-cetyl pyridinium bromide, sodium N-lauroyl sarcosine, N-dhyristoyle glycine and potassium N-lauroyl sarcosine. The sodium salicylate or other analgesics comprise from about 0.1 to about 1% per weight of the rinse formulation.

The dental rinse described in the '758 and '708 patents is an alkaline solution having a pH of at least about 7.5 and above, but not greater than 10. It includes an oral surfactant and detergent builder in a liquid carrier. The liquid carrier may include water or a solution of water and ethanol from about 70% to about 95% of the formulation. Nonionic oral surfactants may include mixtures of laureate esters of sorbitol and sorbitol anhydrides such as Tween 20. In addition, oral surfactants include alkyl sulfonates or sulfates such as sodium lauroyl sulfate or sodium N-lauroyl sarcosinates in concentrations ranging from about 0.1% to about 10% by weight of the composition. Detergent builders are also used such as sodium carbonate, sodium borate or alkaline mixtures of sodium carbonate and/or sodium borate with sodium bicarbonate in concentrations ranging from 0.1% to about 1% by weight of the dental rinse formulation. Additional adjuvant ingredients to provide desirable flavoring, coloring and mouthfeel are included such as the flavorants thymol, eucalyptol or menthol and humectants such as glycerine in amounts up to about 20% which functions as a sweetener and imparts body to the composition. Equivalent materials such as sorbitol or propylene glycol may also be employed. A typical formulation is shown in examples 1 and 3 of the '708 patent.

Neither of the '758 or '708 patents describes the use of a formulation which promote bacterial lysis. Also, both patents require an alkaline pH for their formulations.

Breath freshener compositions including mints, candies, dental creams and mouthwashes are described in U.S. Pat. No. 4,409,202. The active ingredient in this patent is vegetable oil employed in combination with magnesium hydroxide. Example 4 describes a mouthwash formulation which includes magnesium hydroxide and hydrated magnesium carbonate in combination with cottonseed oil, sodium bicarbonate in a concentration of 2.5 grams per 1,000 ml, and glycerine (a humectant) at a concentration of about 42% by weight (420 ml per 1,000 ml). Oral surfactants and detergents are not included in the mouthwash formulations (Examples 4 and 9). A dental cream is described in Example 5, in which sodium lauryl sulfate is used in a concentration of about 1.5 parts by weight. It is important to note that the compositions of the '202 patent are not made for the purpose of effecting cell lysis or cell death of bacteria to destroy plaque, but rather for reducing mouth odor due to ingestion of onions and similar malodorous foods. This is especially evident since such dental creams are highly diluted during use by saliva and water.

A germicide free antibacterial or mouthwash composition is described in U.S. Pat. No. 4,150,151. The composition includes water, ethanol, flavoring such as spearmint or peppermint, and from about 0.1 to about 0.6% alkyl sulfate anionic surfactant mixture such as dodecyl and tetradecyl sulfate salt including sodium lauroyl sulfate, and nonionic emulsifiers may be included up to about 3% by weight. A humectant may also be included in a concentration of up to about 25% by weight for the purpose of better mouthfeel. Also included may be up to 2% by weight of alkaline metal halide, up to about 2% by weight of a buffering salt pair, up to about 2% of a sodium saccharin for a sweetening effect, and a make up quantity of water. The '151 patent does not describe compositions intended to cause cell lysis of oral bacteria.

Various dentifrice formulation for toothpaste or dental creams describe the use of high concentrations of glycerine and other humectants. It is understood that the humectants are required to maintain the moisture and texture of the dental creams or toothpastes to prevent drying out of these compositions. In fact when such compositions are contacted in the mouth, they are diluted to a large extent by saliva and water in the mouth during the brushing process. In particular, U.S. Pat. No. 2,689,170 describes an oral preparation for the inhibition of dental caries which includes a dental cream containing sodium lauroyl sarcosides, calcium carbonate a flavorant and glycerine. The glycerine or other humectant may range from about 5 to 50% by weight. The dilution of the dentifrice formulation with water and saliva in the mouth is described in detail in column 5 of the patent. A mouthwash formulation is described at column 17. Humectants, however, are not described in the compositions of the mouthwash formulation.

Additional dentifrice compositions having high humectant concentrations needed for preventing hardening, such as glycerine or sorbitol at a level from about 15 to about 70% by weight are described in U.S. Pat. No. 4,846,650. The compositions include an anticalculus agent, polyepoxysuccinic acid and its pharmaceutically-acceptable salts. Emulsifying agents, such as sodium alkyl sulfate, are also used in this formulation. In the mouthwash compositions disclosed in the '650 patent, humectants are used in much lower concentrations of up to about 20%, preferably up to about 5% by weight. The humectants are not used in this formulation for anything other than their moistening and mouthfeel properties.

Other dentifrices, chewing gums and toothpastes having high humectant concentration are described in U.S. Pat. Nos. 4,844,883; 4,837,008; 4,824,661; and 4,178,362. None of these patents, however, describes an oral composition for the lysis of oral bacteria and plaque.

The inventor herein, in U.S. Pat. Nos. 4,618,489 and 4,861,582 describes the use of inorganic monovalent anions in mouthrinse formulations to show that these anions would activate bacteriolysis of plaque pathogens involved in the oral diseases, such as caries, gingivitis and periodontitis. However, while limited reductions in caries and gingivitis were seen in clinical trials with an optimal salt mouthrinse formulation, it became clear that (i) not all plaque bacteria were lysed by this inorganic salt combination in vitro or in vivo, (ii) these salts by themselves, when used in dentifrice preparations, would not directly activate the bacterial autolytic enzymes; i.e. prior lysozyme damage to the bacteria was required, and (iii) new formulations were required to provide more effective bacteriolysis if significantly better results were desired in the treatment of oral disease.

Accordingly, a feature of the present invention is to provide a composition and method for the treatment of gingivitis and periodontal disease which removes dental plaque and prevents new plaque build up.

Another aspect of the present invention is to provide a composition which causes lysis and cell death of oral bacteria which constitutes and is imbedded in dental plaque.

A further feature of the present invention is to provide a composition which rapidly lyses and kills oral bacteria over a very short periods of exposure.

It is still a further aspect of the present invention to provide a composition for the lysis of oral bacteria which can be made readibly available in an over-the-counter formulation.

SUMMARY OF THE INVENTION

These and other features and aspects are provided by the present invention which describes an antimicrobial composition and particularly a composition for the lysis and killing of microbes in general, and specifically describes oral compositions for the lysis and killing of oral bacteria. The compositions of the present invention include a humectant such as glycerol, sorbitol or comparable compounds and provide an in-mouth concentration of such substances from about 20% to about 80% weight/volume in dentifrice preparations, in particular mouthrinses. These compositions further comprise (a) bicarbonate ion at about 0.5% to about 2% wt./vol. and if desired, thiocyanate, chloride or fluoride ion at about 0.5% to about 2% wt./vol. (b) sodium lauroyl sarcosinate or other anionic detergents from about 0.05% to about 1% wt./vol. and (c) Tween 20 or other non-ionic detergents or structurally similar compounds from about 0.01% to about 3% vol./vol. In addition, alcohol may be added up to a level of 15% vol./vol. along with appropriate sweetening and flavoring agents. Water is then added to 100%.

The compositions may be introduced in a manner and vehicle suitable for oral cavity administration. This invention also relates to a method of using such compositions for treating and inhibiting dental caries, dental plaque and gingivitis, oral malodor and periodontopathic conditions in mammals, particularly humans, in need of anti-caries, anti-plaque, anti-gingivitis, anti-malodor or anti-periodontopathic therapy. The compositions of the present invention are conventionally formulated into mouthrinses (mouth washes) and the commonly utilized dentifrice treatment agents, that is, dental creams, toothpastes and toothpowders, as well as into typically chewed carriers such as gums, lozenges and candies.

BRIEF DESCRIPTION OF THE DRAWINGS

FIG. 1 is a graph illustrating the effect of glycerin and antibacterial agents on cell lysis (bacteriolytic activity) of the bacterium *Lactobacillus casei* DSM.

Figure 2:
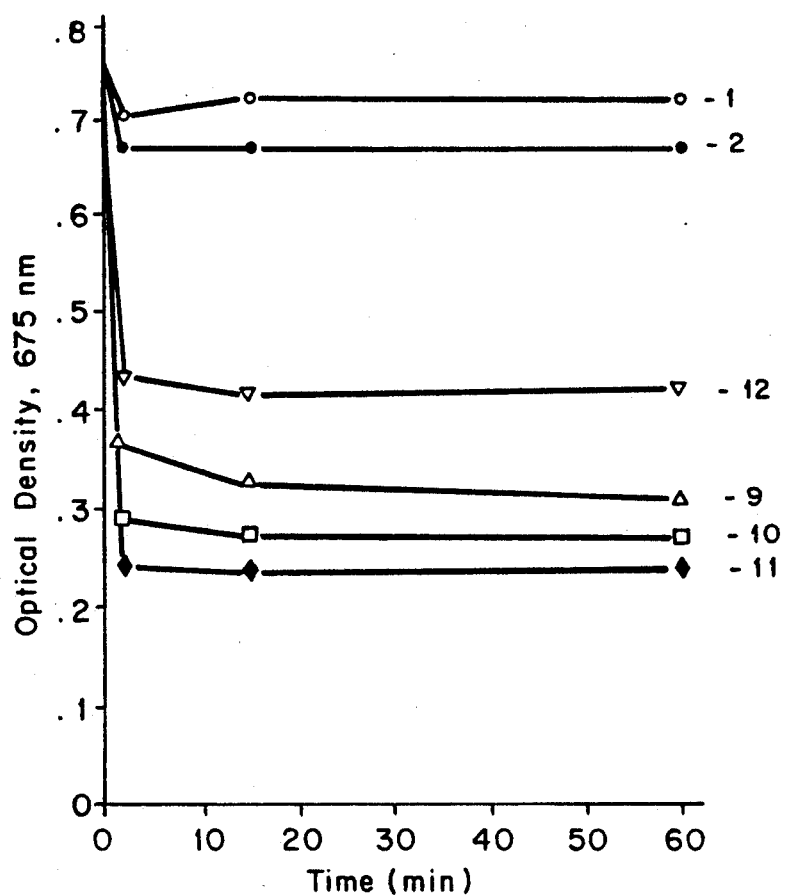
FIG. 2 is a graph illustrating the effect of glycerin containing mouthrinses on cell lysis of the bacterium *Streptococcus sanquis* 10557.

*actinomycetemcomitans* by bicarbonate and by the preferred bacteriolytic mouthrinse composition of the present invention.

DETAILED DESCRIPTION OF THE INVENTION

The present invention is directed to the preparation of compositions adapted for the lysis of oral bacteria. These compositions provide anticariogenic (for example, lysis of *Streptococcus mutans* and *Lactobacillus casei*) antiplaque-antigingivitis (for example, lysis of *Streptococcus sanquis* types I and II, *Streptococcus mitis*, *Staphylococcus epidermidis*, *Actinomyces viscosus*, *Actinomyces naeslundii*, *Haemophilus parainfluenza*, *Neisseria sicca*, *Veillonella dispar* and *Fusobacterium nucleatum*), antimalodor (primarily, *Fusobacterium nucleatum* and *Bacteriodes gingivalis*) and antiperiodontopathic (for example lysis of *Fusobacterium nucleatum*, *Capnocytophaga gingivalis*, *Bacteroides gingivalis*, *Actinobacillus actinomycetemcomitans* and *Eikenella corrodens*) therapy. It should be noted that this list of bacteria which is lysed by the composition of the present invention is not considered exhaustive, but merely illustrative.

The compositions of the present invention include a humectant such as glycerol, sorbitol or comparable compounds and provide an in-mouth concentration of such substances from about 20% to about 80% weight/volume in dentifrice preparations, in particular mouthrinses. These compositions further comprise (a) bicarbonate ion at about 0.5% to about 2% wt./vol. and if desired, thiocyanate, chloride or fluoride ion at about 0.5% to about 2% wt./vol. (b) sodium lauroyl sarcosinate or other anionic detergents from about 0.05% to about 1% wt./vol. and (c) Tween 20 or other non-ionic detergents or structurally similar compounds from about 0.01% to about 3% vol./vol. In addition, alcohol may be added up to a level of 15% vol./vol. along with appropriate sweetening and flavoring agents. Water is then added to 100%.

The compositions may be introduced in a manner and vehicle suitable for oral cavity administration. This invention also relates to a method of using such compositions for treating and inhibiting dental caries, dental plaque and gingivitis, oral malodor and periodontopathic conditions in mammals, particularly humans, in need of anti-caries, anti-plaque, anti-gingivitis, antimalodor or anti-periodontopathic therapy. The compositions of the present invention are conventionally formulated into mouthrinses (mouth washes) and the commonly utilized dentifrice treatment agents, that is, dental creams, toothpastes and toothpowders, as well as into typically chewed carriers such as gums, lozenges and candies.

The preferred embodiment of the present invention is an oral rinse having agents which cause lysis of oral bacteria. Briefly, the oral rinse may be used for the lysis of a broad spectrum of bacteria in the mouth, used either as a mouthwash or dispensed in a device such as WATERPIK ® below the gingival margin.

The key to the lytic action of the mouthwash composition is the use of a humectant such as glycerol or sorbitol in the preferred range of from about 30% to about 50% wt./vol., or on a broad in-mouth range of from about 20% to 80% wt./vol. The mouthwash also contains bicarbonate ions from about 0.5% to about 2% wt./vol. and optionally thiocyanate, chloride or fluoride ions as an anti-caries ingredient from about 0.5% to about 2% wt./vol. An anionic detergent is also required such as sodium lauroyl sarcosinate or other anionic detergents such as sodium lauroyl sulfate in the range of from about 0.05% to about 1% wt./vol. preferably about 0.4% wt./vol.; and non-ionic detergents or structurally similar compounds such as Tween 20 in a range of from about 0.01% to about 3% vol./vol., preferably about 1% vol./vol. Other ingredients could include alcohol at about up to 15% vol./vol., appropriate sweetening and flavoring agents and water added to make up the remaining 100%.

It is postulated that the high percentage of the humectants cause swelling of bacterial cells resulting in partial separation of bacterial cell membrane from the bacterial cell wall. In this process, enzymes in the bacterial called autolysins, located at the juncture of the cell membrane and cell wall became suceptible to deregulation by activating agents such as inorganic monovalent anions or detergents, and are probably activated. The autolysins hydrolyze chemical bonds in the cell wall and produce holes in the bacterial cell membranes. Normally, these autolysins are important to the bacterial for growth and division, but once deregulated and activated they cause bacterial suicide. The combination of the humectants with lytic facilitation in the mouthwash composition (i.e. bicarbonate), and in the saliva, causes massive cell lysis and cell death. The massive lysis and death of bacteria constituting plaque leads to the destruction and elimination of the plaque.

In the mouth, bacteria are bathed by saliva and salivary lysing agents (lysozymes) which interact with and damage the bacteria. The bacteria, swelled by the humectants and damaged by saliva allow penetration of bicarbonate and detergents into the cell, deregulating and activating the bacterial autolysins. Thus, once the bicarbonate and detergents penetrate the cells, massive cell lysis occurs. By themselves, however, these humectants do not cause bacterial lysis, rather the bacteria seem to remain alive and even grow if lytic activating agents such as Tween, bicarbonate and sodium lauryl sarcosinate have not been included. By contrast, effective lysis by either Tween, bicarbonate or sodium lauroyl sarcosinate, alone or in combination, is not observed unless humectants are present at high concentrations.

The compositions of the present invention facilitate maximal lysis of oral bacteria by using an inmouth concentration (i.e. 20–80% wt./vol.) of the humectant (e.g., glycols, sugar alcohols, corn syrup, etc.) in dentifrice preparations. Humectants normaly provide body and consistency to the formulation and also a smooth, pleasant feel upon swirling or brushing in the mouth. However, the level of the humectant, for example, glycerol or sorbitol alone is not enough to effect lysis of the bacteria, rather, this key ingredient facilitates lysis upon addition of other agents, such as, inorganic monovalent anions (for example, bicarbonate and thiocyanate), anionic surfactant detergents (for example sodium lauroyl sulfate or sodium lauroyl sarcosinate) or non-ionic surfactant detergents (for example, Tweens or polymers of polyoxyethylene and polypropylene).

It is noteworthy that neither the inorganic monovalent anions nor the anionic detergents, nor the nonionic detergents by themselves have any effect on cell lysis but require high concentrations of the humectant lytic facilitator. Moreover, the experimental data clearly shows that maximal synergistic lysis and cell death are achieved only when the lytic facilitator is present with all three (inorganic monovalent anions, anionic detergents and nonionic detergents) types of lytic activators in one formulation. In contrast to the action of inorganic/monovalent anion deregulation of bacterial autolytic enzymes which when used alone in dentifrice preparations require prior lysozyme cell damage, the highly effective lytic compositions of the present invention also cause deregulation of the autolysins and lysis of the cell directly, even in the absence of prior lysozyme damage. These new compositions, therefore, allow maximal lysis and provide a distinct advantage, in that to facilitate lysis the dental plaque does not have to be covered by salivary lysozyme and salivary proteases, which may in fact be present in saliva, albeit in limited concentrations.

In the forgoing examples, the superior bacteriolytic properties of the preferred compositions of the present invention were demonstrated by both standardized in vitro assay procedures involving both the cell lysis and cell death of the bacteria and also by in vivo human clinical studies. The lysis was assayed by spectrophotometric reductions in turbidity of bacterial cell suspensions (illustrated in FIGS. 1–8) and cell death was measured by the number of surviving bacterial colony forming units compared to untreated controls plated onto appropriate agar media (shown in Tables 1–10). When a drop in the turbidity of cell suspensions is accompanied by cell death, the lysis was confirmed by assaying the release of tritiated intracellular nucleic acid, and in come cases by electron microscopy. In vivo determinations were performed for the efficacy of the compositions of the present invention as anti-plaque and anti-gingivitis mouthrinses compared to water, bicarbonate and other controls.

EXAMPLES

I. In Vitro Studies

A. Materials and Methods

The oral bacteria used in these examples were either isolated from lesion sites in the mouth or were purchased from the American Type Culture Collection (Rockville, Md.).

Bacteria were grown from lyophilized cultures in their respective bacteriological media to the late log phase of growth. After transfer to fresh media, growth was allowed to proceed to late log phase. Bacterial cells were harvested and washed once in distilled water.

During the bacterial harvesting and washing procedure, whole saliva (50 to 70 milliliters) was collected by stimulation with paraffin wax. The saliva was adjusted to pH 4.5 to stabilize the lysozyme activity and was left on ice for 20 minutes. The saliva was centrifuged to yield the salivary supernatant which was adjusted to pH 5.3 for lytic assays of gram-positive bacteria and also to pH 7.0 for gram-negative bacteria.

Pelleted bacteria were suspended in the salivary supernatant for a period of 90 minutes (for gram-positive bacteria) and 30 minutes (for gram-negative bacteria). After the incubation period, salivary suspensions were distributed into 2.5 ml aliquots in screw cap tubes and centrifugation was carried out. Cell pellets were then rapidly resuspended in the various mouthrinses and optical densities (turbidities) at 675 nm were immediately measured and followed for a period of up to 1 hour incubation at 37° C. In the first minute, aliquots of 100 microliters of each mouthrinse suspension were removed and diluted into 900 ul of bacteriological media ($10^{-1}$ dilution). Serial dilutions were then made through $10^{-6}$ and from each dilution, 100 ul was removed and plated onto the respective agar containing bacteriological medias. Agar plates were allowed to incubate for 48 to 72 hours either aerobically or anaerobically and bacterial colonies were counted. Each mouthrinse was compared for effects on bacterial turbidities and viabilities (colony forming units) to control treatment of bacterial pellets suspended in distilled water.

Lysis was confirmed by radioactive thymidine assays according to methodologies described in U.S. Pat. Nos. 4,618,489 and 4,861,582, the disclosure of both patents are incorporated by reference herein. Lysis was also measured in the absence of saliva treatment; that is, distilled water replaced the 30 minute or 90 minute treatment of the freshly grown bacteria, prior to either the water control or mouthrinse treatment.

Prior Experiments

Previous results have shown that bicarbonate in combination with one or more of thiocyanate, chloride or fluoride ions results in synergistic lysis of selective bacterial species (see U.S. Pat. Nos. 4,618,489 and 4,861,581; and Pollock et al. *Journal of Dental Research*, 66, 467–474 (1987)). Among these selective bacteria, *Streptococcus mutans*, the main causative organism responsible for dental caries is lysed by inorganic monovalent anions through the salivary lysozyme-protease bacteriolytic activation of autolytic enzymes both in *vitro* (Pollock et al., *Journal of Dental Research*, 66, 467–474 (1987) and *in vivo* (Pollock et al., *Infection and Immunity*, 45, 610–617 (1984)). Among the lactobacilli, which are also cariogenic bacteria, *Lactobacillus plantarum* is easily lysed by inorganic monovalent anions; however, *Lactobacillus casei*, for reasons unknown, is not lysed to any great extent in the presence of saliva.

EXAMPLE 1

FIG. 1 is a graph illustrating the effect of varying glycerin concentrations with and without antibacterial agents on cell lysis of *Lactobacillus casei* DSM. As can be seen in FIG. 1 the line having the lowest optical density is x, illustrating a preferred mouthrinse formulation (Test Agent #5) containing 40% glycerin (or sorbitol)+3% Tween 20+7.5% ethanol+1.5% sodium bicarbonate+0.5% sodium thiocyanate. These results are compared to those shown in Table 1 for the same formulations. While FIG. 1 shows that the combination of sodium bicarbonate and sodium thiocyanate has some effect on reducing the optical density (decreasing the turbidity in effect to lyse the cell) of *Lactobacillus casei* in agreement with earlier findings.

TABLE 1

| | Effect of Glycerin and Antibacterial Agents on Cell Death (Bacteriocidal Activity) of *Lactobacillus Casei* DSM | | |
|---|---|---|---|
| Test Agent # | Mouthrinse | Bacterial Colony Forming Units per milliliter after treatment | % Inhibition Compared to Control |
| 1 | Water control | $2.3 \times 10^9$ | — |
| 2 | 40% glycerin or sorbitol | $3.2 \times 10^9$ | 0 |

TABLE 1-continued

Effect of Glycerin and Antibacterial Agents on Cell Death
(Bacteriocidal Activity) of *Lactobacillus Casei* DSM

| Test Agent # | Mouthrinse | Bacterial Colony Forming Units per milliliter after treatment | % Inhibition Compared to Control |
|---|---|---|---|
| 3 | 1.5% sodium bicarbonate + 0.5% sodium thiocyanate | $1.4 \times 10^9$ | 39 |
| 4 | 20% glycerin or sorbitol + 3% Tween 20 + 7.5% ethanol + 1.5% sodium bicarbonate + 0.5% sodium thiocyanate | $2.0 \times 10^6$ | >99.9 |
| 5 | 40% glycerin or sorbitol + 3% Tween 20 + 7.5% ethanol + 1.5% sodium bicarbonate + 0.5% sodium thiocyanate | 0 | 100 |

However, lysis and cell death of L. casei cells, whether pre-treated first with saliva or water, can be accomplished by adding glycerol or sorbitol in the presence of lytic activating agents (see Test Agent #4, Table 1). Optical density reductions are observed to be dependent upon the concentration of humectant (FIG. 1); however, neither glycerin nor sorbitol alone leads to cell death, as evidenced by no change (in fact, increase in growth is noted) in colony forming units (Test Agent #2, Table 1). The data in FIG. 1 and Table 1 suggest that the inorganic monovalent anions (bicarbonate and thiocyanate) are one type of lytic activator; however, the complete killing of the L. casei bacteria within one minute by a mouthrinse containing 40% glycerin or 40% sorbitol (Table 1) with the additional ingredients suggests that agents other than the inorganic monovalent anions, are lytic activators.

FIG. 1 also demonstrates that the mouthrinse containing 40% glycerin or sorbitol is significantly more effective in promoting cell lysis (larger drop in optical density or turbidity) than a mouthrinse containing only 20% glycerin or sorbitol. A comparison of the killing activity of the two mouthrinses further indicates that the 40% humectant concentration is superior to the 20% concentration of humectant, as there are still surviving L. casei microbes with the lesser concentration (Table 1).

EXAMPLE 2

FIG. 2 shows the effect of glycerin containing mouthrinses at varying glycerine concentrations on cell lysis of *Streptococcus sanguis* 10557. A preferred formulation (Test Agent #11, Table 2) contained 40% glycerin + 3% Tween 20 + 1.5% ethanol + 1.5% sodium bicarbonate + 0.5% sodium thiocyanate + 0.5% sodium lauroyl sulfate produced the most dramatic results.

TABLE 2

Effect of Glycerin Concentration on Cell Death of *Streptoccocus sanguis* 10557 in the Presence or Absence of Tween 20

| Test Agent # | Mouthrinse | Bacterial Colony Forming Units per milliliter after treatment | % Inhibition Compared to Control |
|---|---|---|---|
| 1 | Water control | $1.00 \times 10^9$ | — |
| 2 | 1.5% sodium bicarbonate + 0.5% sodium thiocyanate | $0.92 \times 10^9$ | 8 |
| 3 | 10% glycerin | $0.80 \times 10^9$ | 20 |
| 4 | 10% glycerin + 3% Tween 20 | $0.75 \times 10^9$ | 25 |
| 5 | 20% glycerin | $0.90 \times 10^9$ | 10 |
| 6 | 20% glycerin + 3% Tween 20 | $0.64 \times 10^9$ | 36 |
| 7 | 30% glycerin | $1.23 \times 10^9$ | 0 |
| 8 | 30% glycerin + 3% Tween 20 | $0.30 \times 10^9$ | 70 |
| 9 | 40% glycerin | $2.24 \times 10^9$ | 0 |
| 10 | 40% glycerin + 3% Tween 20 | $0.13 \times 10^9$ | 87 |
| 11 | 40% glycerin + 3% Tween 20 + 7.5% ethanol + 1.5% sodium bicarbonate + 0.5% sodium thiocyanate + 0.5% sodium lauroyl sulfate | $0.10 \times 10^6$ | >99.9 |
| 12 | 20% glycerin + 3% Tween 20 + 7.5% ethanol + 1.5% sodium bicarbonate + 0.5% sodium thiocyanate + 0.5% sodium lauroyl sulfate | $0.10 \times 10^9$ | 90 |

While FIG. 2 and Table 2 show that bicarbonate and thiocyanate have little if any effect on cell lysis and cell death of *Streptococcus sanguis*, Tween 20, a non-ionic detergent is effective in activating cell lysis and death of this microbe. Some killing is observed with 10% and 20% glycerin (Table 2) but at 30% and 40% glycerin, enhancement of growth is noted unless Tween 20 is added to the glycerin (Table 2). Compared to Test Agent #10 (Table 2), the 40% glycerin+3% Tween 20 combination, (Test Agent #11, Table 2), 40% glycerin+inorganic monovalent anions+Tween 20+other ingredients, is far superior in causing cell death. The latter findings with the preferred formulation (Test Agent #11, Table 2) suggests that still another type of agent is important in the cell death process. FIG. 2 shows that Test Agent #11 is more effective in lysing or reducing the optical density of *S. sanguis* than Test Agent #10 or Test Agent #9 (40% glycerin alone) or Test Agent #12 (20% glycerin mouthrinse). Noteworthy, the 20% glycerin mouthrinse (Test Agent #12) is significantly less effective than the preferred 40% glycerin mouthrinse, (Test Agent #11) in killing *S. sanquis* (Table 2).

EXAMPLE 3

Figure 3:
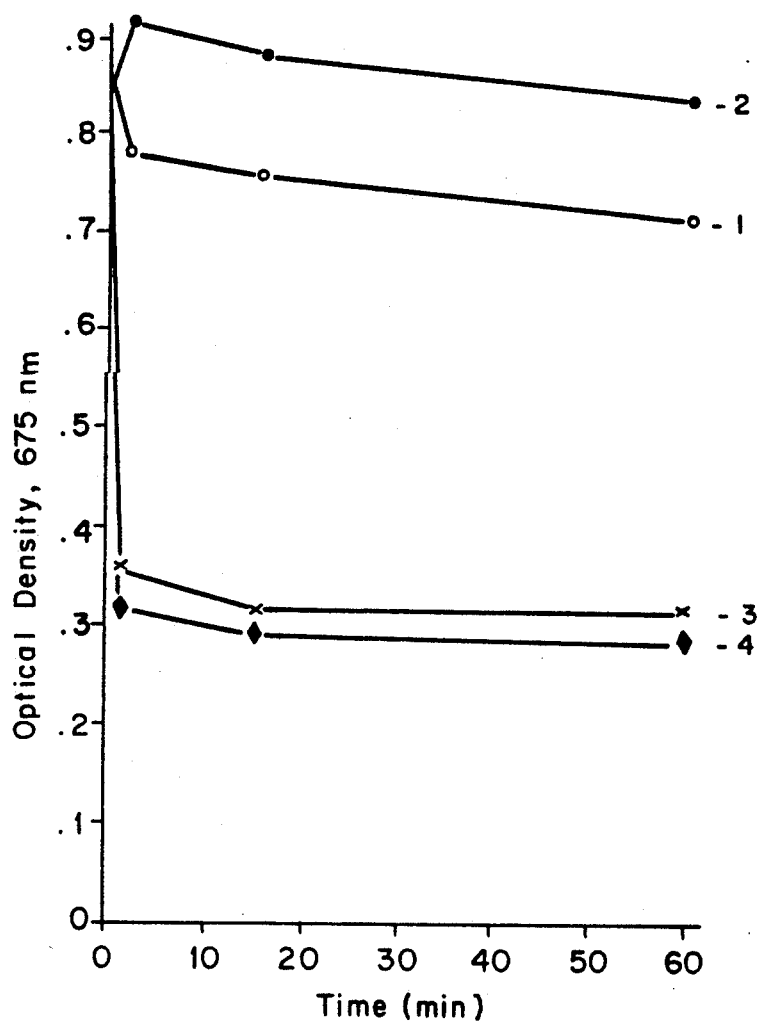
FIG. 3 is a graph illustrating the effect of sodium lauryl sulfate on cell lysis of *Streptococcus mitis* 905.

FIG. 3 and Table 3 show the effect of sodium lauroyl sulfate on cell lysis and cell death of *Streptococcus mitis* 905. As shown in FIG. 3 and Table 3, the most dramatic results are observed in using a preferred composition containing 40% glycerin 3% Tween 20+7.5% ethanol+1.5% sodium bicarbonate+0.5% sodium thiocyanate+0.5% sodium lauroyl sulfate. FIG. 3 shows that the third type of lytic activating agent for use in the preferred composition is an anionic surfactant, for example, sodium lauroyl sulfate which, when added to the mouthrinse, further enhances the cell lysis of *Streptococcus mitis*.

EXAMPLE 4

Figure 4:
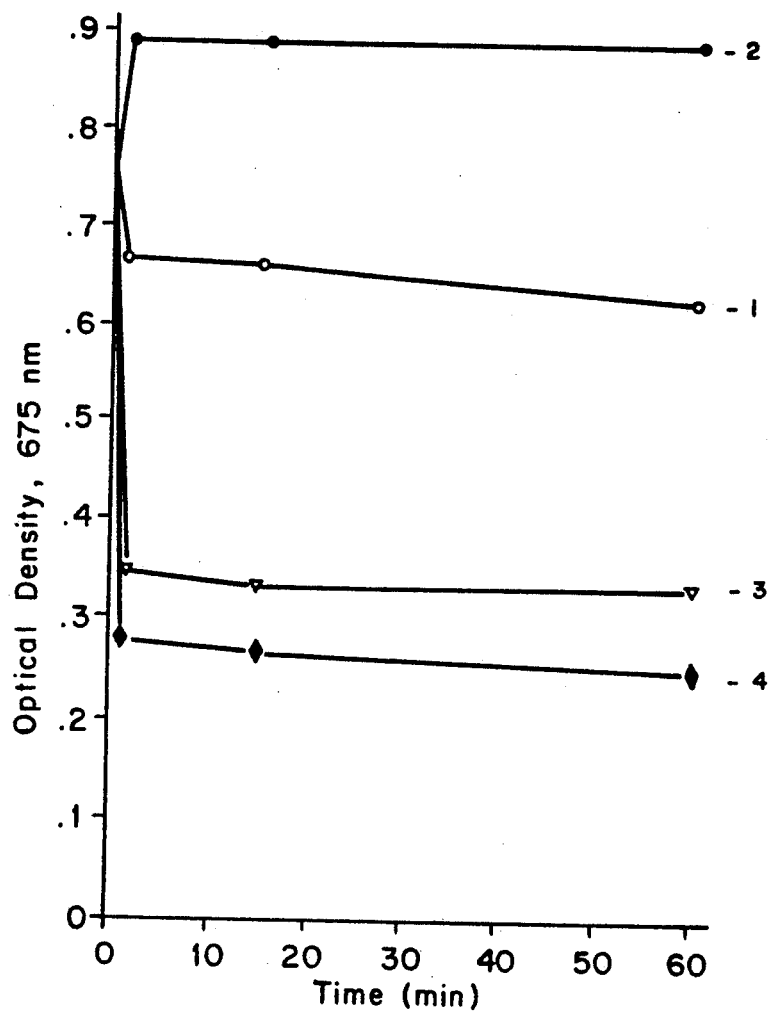
FIG. 4 illustrates the effect of mouthrinses on cell lysis of *Actinomyces naeslundii*.

FIG. 4 and Table 4 illustrate that combinations of 40% glycerin+3% Tween 20+0.5% sodium lauroyl sulfate are not as effective in either maximally lysing or killing of *Actinomyces naeslundii* 19039 as when these ingredients are present together along with inorganic monovalent anions (preferred composition #4, Table 4). The data also suggests that although sodium lauroyl sulfate is an effective killing agent (see Table 4), it by itself does not decrease turbidity of the cell culture, and therefore does not promote cell lysis unless present with a lytic facilitator.

EXAMPLE 5

Figure 5:
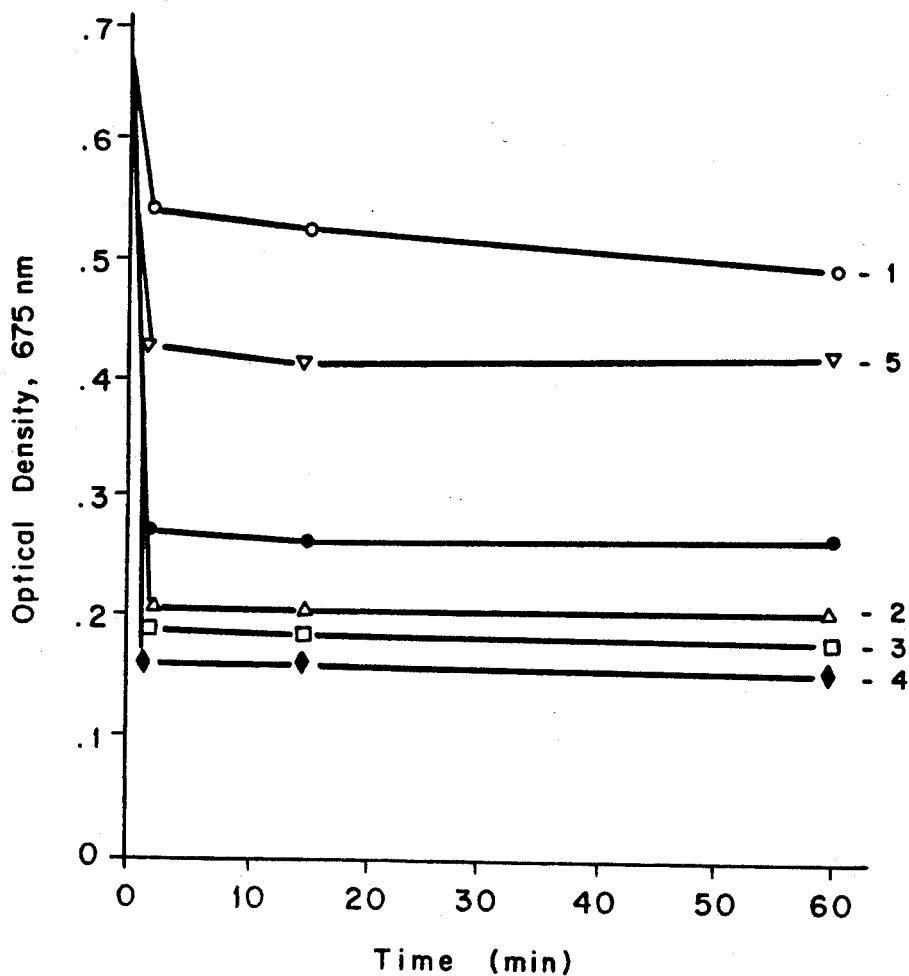
FIG. 5 illustrates the effect of Tween 20 concentrations on cell lysis of *Antinomyces viscosus*.

FIG. 5 shows the effect of various Tween 20 concentrations in the preferred composition of the present invention on cell lysis of *Actinomyces viscosus* 19246, and compares those effects with those obtained using a commercially available mouthrinse PLAX. The most dramatic effects are for preferred composition (Test Agent #4) containing 40% glycerin+1% Tween 20+7.5% ethanol+1.5% sodium bicarbonate+0.5% sodium thiocyanate+1% sodium lauroyl sulfate. FIG. 5 and Table 5 show that Tween 20 displays a concentration dependence for both bacteriolysis (FIG. 5) and cell death (Table 5) of *Actinomyces viscosus*.

TABLE 3

Effect of Sodium Lauroyl Sulfate on Cell Death of *Streptococcus mitis* 905

| Test Agent # | Mouthrinse | Bacterial Colony Forming Units per milliliter after treatment | % Inhibition Compared to Control |
|---|---|---|---|
| 1 | Water control | $2.0 \times 10^8$ | — |
| 2 | 0.5% sodium lauroyl sulfate | 0 | 100 |
| 3 | 40% glycerin + 3% Tween 20 + 7.5% ethanol + 1.5% sodium bicarbonate + 0.5% sodium thiocyanate | $1.0 \times 10^7$ | 95 |
| 4 | 40% glycerin + 3% Tween 20 + 7.5% ethanol + 1.5% sodium bicarbonate + 0.5% sodium thiocyanate + 0.5% sodium lauroyl sulfate | 0 | 100 |

Table 3 confirms that the addition of sodium lauroyl sulfate to the mouthrinse (compare preferred Test Agent #4 with Test Agent #3) significantly enhances the killing of this bacterium. Although this anion surfactant alone is effective in killing *S. mitis* (see composition #2, Table 3), FIG. 3 shows that the sodium lauroyl sulfate by itself does not decrease turbidity of the cell suspension, and therefor does not promote cell lysis unless present with a lytic facilitator.

TABLE 4

Effect of Mouthrinses on Cell Death of *Actinomyces naeslundii* 19039

| Test Agent # | Mouthrinse | Bacterial Colony Forming Units per milliliter after treatment | % Inhibition Compared to Control |
|---|---|---|---|
| 1 | Water control | $1.6 \times 10^7$ | — |
| 2 | 0.5% sodium lauroyl sulfate | 0 | 100 |
| 3 | 40% glycerin + 3% Tween 20 + 0.5% sodium lauroyl sulfate | $8 \times 10^5$ | 95 |
| 4 | 40% glycerin + 3% Tween 20 + 0.5% sodium lauroyl sulfate + 7.5% ethanol + 1.5% sodium bicarbonate + 0.5% sodium thiocyanate | 0 | 100 |

TABLE 5

Effect of Tween 20 Concentration on Cell Death of *Actinomyces viscosus* 19246

| Test Agent # | Mouthrinse | Bacterial Colony Forming Units per milliliter after treatment | % Inhibition Compared to Control |
|---|---|---|---|
| 1 | Water control | $84 \times 10^7$ | — |
| 2 | 40% glycerin + 1% Tween 20 + 7.5% ethanol + 1.5% sodium bicarbonate + 0.5% sodium thiocyanate + 1.0% sodium lauroyl sulfate | $10 \times 10^7$ | 88.1 |
| 3 | 40% glycerin + 2% Tween 20 + 7.5% ethanol + 1.5% sodium bicarbonate + 0.5% sodium thiocyanate + 1.0% sodium lauroyl sulfate | $5 \times 10^7$ | 94.1 |

TABLE 5-continued

| | Effect of Tween 20 Concentration on Cell Death of *Actinomyces viscosus* 19246 | | |
|---|---|---|---|
| Test Agent # | Mouthrinse | Bacterial Colony Forming Units per milliliter after treatment | % Inhibition Compared to Control |
| 4 | 40% glycerin + 3% Tween 20 + 7.5% ethanol + 1.5% sodium bicarbonate + 0.5% sodium thiocyanate + 1.0% sodium lauroyl sulfate | $1 \times 10^7$ | 98.8 |
| 5 | PLAX | $46 \times 10^7$ | 45.2 |

Increasing the concentrations of this nonionic detergent increases both lysis and killing of the organism (FIG. 5, Table 5). Also of interest is the observed poor lysis of this organism by the commercial mouthrinse, PLAX (Test Agent #5, FIG. 5) which is described in U.S. Pat. Nos. 4,666,708 and 4,657,758. PLAX is shown to be significantly less effective in lysing and killing this major plaque species (Table 5) as well as other microbes (data not shown) when compared to the mouthrinses of the present invention.

EXAMPLE 6

Table 6 compares the effect of variations in the concentration of ionic detergents in mouthrinses made in accordance with the present invention. Basic mouthrinse I contains 40% glycerol+3% Tween 20+7.5% ethanol+1.5% sodium bicarbonate+0.5% sodium thiocyanate. Basic mouthrinse II contains 30% sorbitol+1% Tween 20+7.5% ethanol+1.5% sodium bicarbonate+0.5% sodium thiocyanate. As shown in Table 6, the level of cell death of this microbe is also dependent on the anionic detergent concentration (compare Test Agent #2 with #3 or Test Agents #4, 5, 6, 7, 8, 9 to each other). Table 6 also shows that sorbitol is more effective than glycerol (compare Test Agents #2 and 3 with Test Agent #10) in promoting cell death, although both appear equally effective in promoting cell lysis. In addition, sodium lauryl sarcosinate, an anionic surfactant detergent, appears to be equally effective as sodium lauryl sulfate. The sarcosinate salt is preferred over the sulfate, since the sarcosinate permits greater stability at lower temperatures with less oral toxicity.

EXAMPLE 7

Table 7 shows the effect of variations in pH of the mouthrinse of the present invention on cell death of *Actinomyces viscosus* 15987. As shown in Table 7, cell death is also dependent on pH. Although higher antimicrobial activity is seen at pH 6 (lauroyl sarcosine acid form), the stability of lauroyl sarcosinate is known to be better at alkaline pH. The formulations could therefore be used within a broad pH range.

EXAMPLE 8

Figure 6:
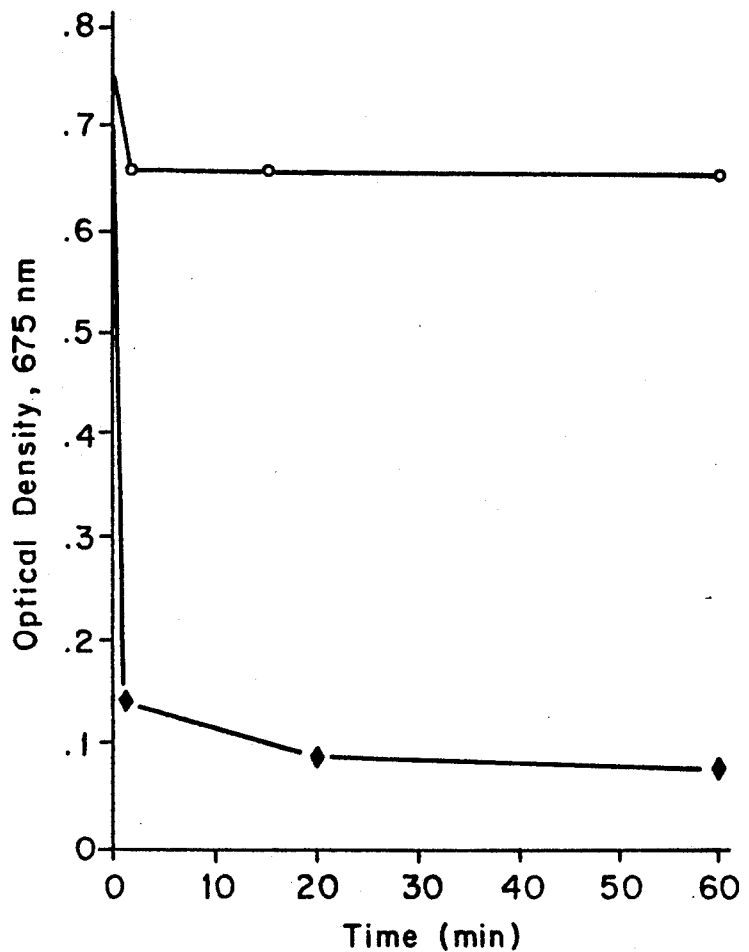
FIG. 6 is a graph showing a typical example of cell lysis of a gram-negative plaque bacterium, *Haemophilus parainfluenza*, by the preferred bacteriolytic mouthrinse of the present invention.
Figure 7:
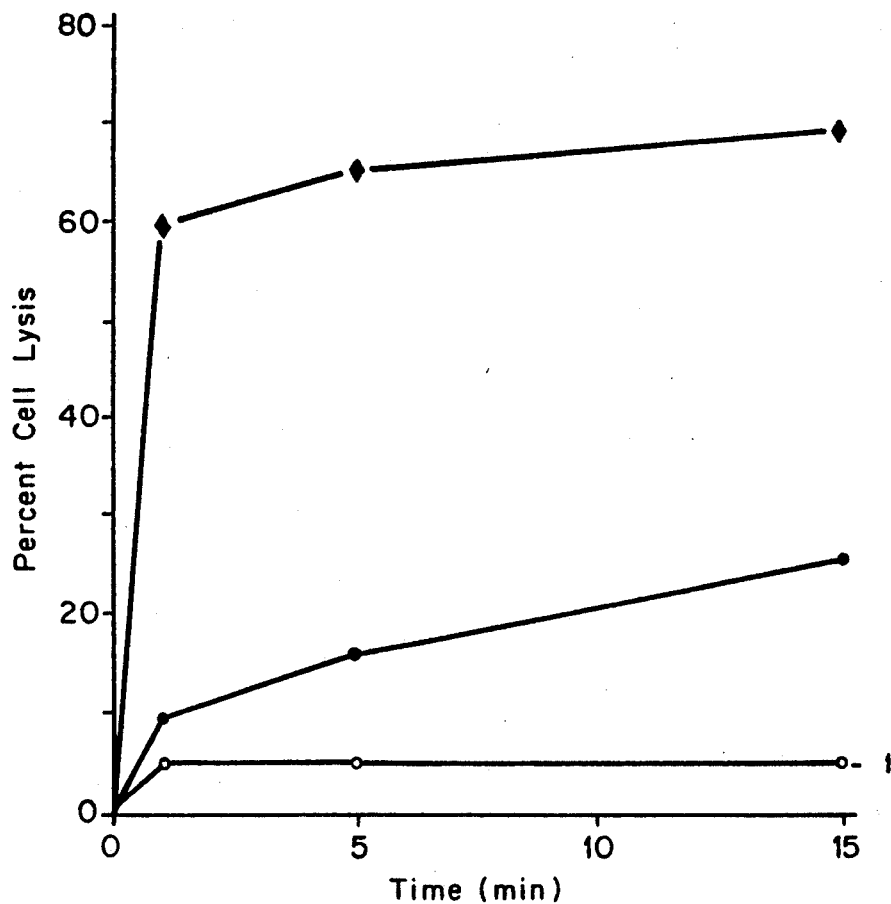
FIG. 7 is a graph illustrating cell lysis of a gram-negative periodontopathic odor causing bacterium, *Fusobacterium nucleatum* by bicarbonate and the preferred bacteriolytic mouthrinse of the present invention.
Figure 8:
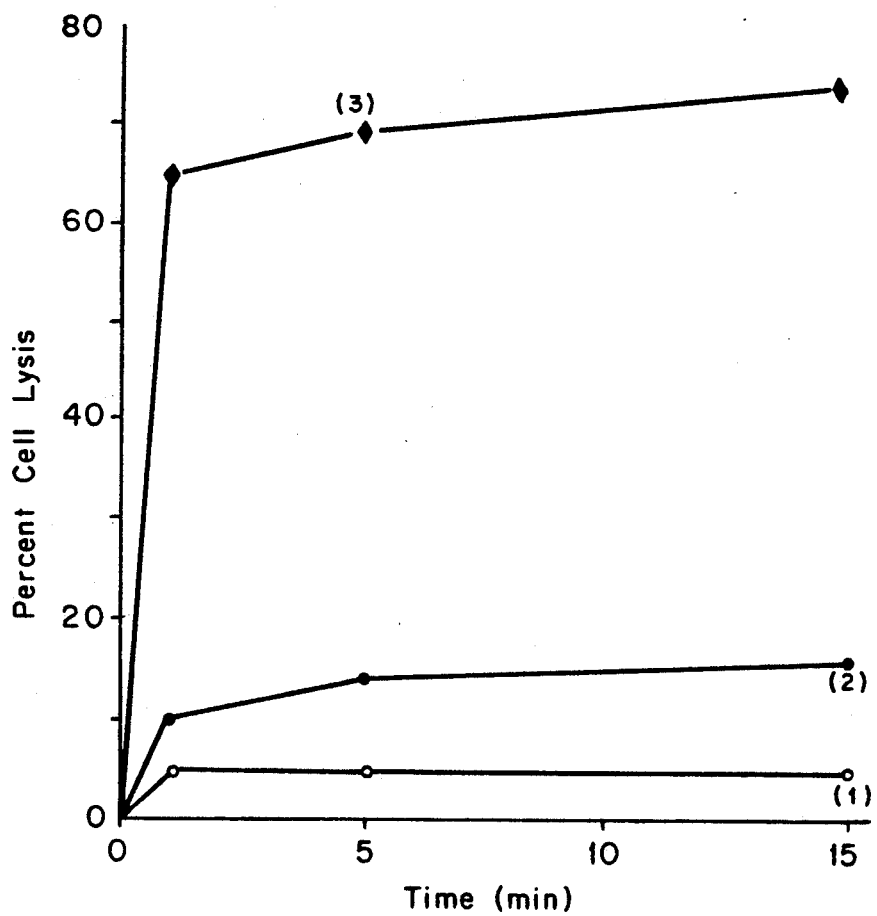
FIG. 8 is a graph illustrating the cell lysis of a gram-negative periodontopathic bacterium, *Actinobacillus*

FIG. 6 illustrates that the mouthrinse combination is effective in lysing typical gram-negative dental plaque microbes such as *Haemophilus parainfluenze*. FIG. 7 and Table 8 show the effects of two preferred mouthrinse compositions of the present invention on gram-negative periodontopathic odor causing bacterium *Fusobacterium nucleatum*. As can be seen in FIG. 7 and Table 8, both preferred mouthrinses can both maximally lyse *Fusobacterium nucleatum*, a gram-negative bacterium implicated in oral malodor, gingivitis and periodontal disease. Lysis of *Fusobacterium nucleatum* is extremely rapid so that within the first minute of testing, 100 percent of the cells are destroyed by the mouthrinse (see Table 8). The same is true for *Bacteriodes gingivalis* (data not shown) and for *Acinomyces actinomycetemcomitans* (shown in FIG. 8 and Table 9), a pathogen involved in causing juvenile periodontitis.

EXAMPLE 9

Further in vitro experiments (data not shown) indicate that the ethanol concentration present in the for-

TABLE 6

| | Effect of Anionic Detergents in Glycerol and Sorbitol Mouthrinses on Cell Death of *Actinomyces viscosus* 19246 | | |
|---|---|---|---|
| Test Agent # | Mouthrinse | Bacterial Colony Forming Units per milliliter after treatment | % Inhibition Compared to Control |
| 1 | Water control | $110 \times 10^6$ | — |
| 2 | Basic Mouthrinse I* + 0.5% sodium lauroyl sulfate | $73 \times 10^6$ | 33.6 |
| 3 | Basic Mouthrinse I + 1.0% sodium lauroyl sulfate | $9 \times 10^6$ | 91.8 |
| 4 | Basic Mouthrinse II** + 0.05% sodium lauroyl sarcosinate | $23.4 \times 10^6$ | 76.6 |
| 5 | Basic Mouthrinse II + 0.1% sodium lauroyl sarcosinate | $4.4 \times 10^6$ | 96.0 |
| 6 | Basic Mouthrinse II + 0.2% sodium lauroyl sarcosinate | $0.7 \times 10^6$ | 99.4 |
| 7 | Basic Mouthrinse II + 0.3% socium lauroyl sarcosinate | $1.2 \times 10^4$ | >99.9 |
| 8 | Basic Mouthrinse II + 0.4% sodium lauroyl sarcosinate | 0 | 100 |
| 9 | Basic Mouthrinse II + 0.5% sodium lauroyl sarcosinate | 0 | 100 |
| 10 | Basic Mouthrinse II + 0.5% sodium lauroyl sulphate | 0 | 100 | mulation does not play a role in either lysing or killing of the bacteria.

TABLE 7

Effect of pH of Mouthrinse on Cell Death of *Actinomyces viscosus* 15987

| Test Agent # | Mouthrinse | Bacterial Colony Forming Units per milliliter after treatment | % Inhibition Compared to Control |
|---|---|---|---|
| 1 | Water control | $5 \times 10^6$ | — |
| 2 | Basic Mouthrinse* at pH 8.5 | $4.2 \times 10^6$ | 16 |
| 3 | Basic Mouthrinse adjusted to pH 7.5 | $4.3 \times 10^6$ | 14 |
| 4 | Basic Mouthrinse adjusted to pH 7.0 | $4.4 \times 10^6$ | 12 |
| 5 | Basic Mouthrinse adjusted to pH 6.5 | $4.0 \times 10^6$ | 20 |
| 6 | Basic Mouthrinse adjusted to pH 6.0 | $2 \times 10^6$ | 80 |

*Basic Mouthrinse - 30% sorbitol + 1% tween 20 + 7.5% ethanol + 1.5% sodium bicarbonate + 0.5% sodium thiocyanate + 0.5% sodium lauroyl sarcosinate

TABLE 8

Effect of Antibacterial Mouthrinses on Cell Death of Periodontopathic Odor Causing Bacterium, *Fusobacterium nucleatum*

| Test Agent # | Mouthrinse | Bacterial Colony Forming Units per milliliter after treatment | % Inhibition Compared to Control |
|---|---|---|---|
| 1 | Water control | $7.5 \times 10^6$ | — |
| 2 | 2% sodium bicarbonate | $5.0 \times 10^6$ | 33.3 |
| 3 | 40% glycerin (or 40% sorbitol) + 3% Tween 20 + 7.5% ethanol + 1.5% sodium bicarbonate + 0.5% sodium thiocyanate + 0.5% sodium lauroyl sulfate | 0 | 100 |
| 4 | 30% sorbitol + 1% Tween 20 + 7.5% ethanol + 1.5% sodium bicarbonate + 0.5% sodium thiocyanate + 0.4% sodium lauroyl sarcosinate | 0 | 100 |

TABLE 9

Effect of Antibacterial Mouthrinses on Cell Death of the Periodontopathic Bacterium, *Actinomyces actinomycetemcomitans*

| Test Agent # | Mouthrinse | Bacterial Colony Forming Units per milliliter after treatment | % Inhibition Compared to Control |
|---|---|---|---|
| 1 | Water control | $8.0 \times 10^7$ | — |
| 2 | 2% sodium bicarbonate | $2.2 \times 10^6$ | 97.3 |
| 3 | 40% glycerin (or 40% sorbitol) + 3% Tween 20 + 7.5% ethanol + 1.5% sodium bicarbonate + 0.5% sodium thiocyanate + 0.5% sodium lauroyl sulfate | 0 | 100 |
| 4 | 30% sorbitol + 1% Tween 20 + 7.5% ethanol + 1.5% sodium bicarbonate + 0.5% sodium thiocyanate + 0.5% sodium lauroyl sarcosinate | 0 | 100 |

Radioactive thymidine experiments (data not shown) further show that the preferred combination of lytic facilitator and lytic activating agent in the mouthrinses of the present invention (for example, Test Agents #3 and #4, described in Example 4 at Table 4) cause true lysis of all of the above described bacteria by effecting release of macromolecular DNA from the interior of the cell. The latter can only be accounted for by extensive damage due to explosion of the cell wall and cell membrane (also seen by electron microscopy) making holes large enough in the cell membrane and cell wall for the DNA to escape. Furthermore, the experimental evidence would suggest that all of the lytic activating agents, anionic and nonionic surfactant detergents and inorganic monovalent anions, when present with sufficient concentrations of humectant lytic facilitator, can cause direct activation of autolytic enzymes in the absence of prior saliva treatment (therefore without prior salivary lysozyme damage).

2. In Vivo Experiments—Clinical Studies

Human clinical studies were performed with volunteers in cross-over testing where the same patients used both water and the lytic mouthrinses at different time periods during the same study. Two clinical trials were conducted.

EXAMPLE 10

The following preferred dental mouthrinse was formulated in accordance with the present invention.

TABLE 10

Components of the Preferred Dental Mouthrinse formulation of Example 10, based on a total volume of 100 ml.

| Component | Concentration |
|---|---|
| Glycerin | 40 gm |
| Tween 20 | 1.0 ml |
| Sodium Bicarbonate | 1.5 gm |
| Sodium Thiocyanate | 0.5 gm |
| Sodium Lauroyl Sulfate | 1.0 gm |
| Alcohol | 7.5 ml |
| Distilled water q.s. | 100 ml |

There were seven patients in the initial trial which was conducted over a two-week period. Forty-eight hours prior to their first visit for clinical examination of dental plaque and gingivitis (Week 0), patients were instructed not to brush their teeth but were asked to rinse their mouth for one minute with one tablespoon (approximately 15 ml) of water in the morning and at bedtime. Subsequently, the patients were instructed to brush their teeth for five complete days (morning and night) and also on the morning of the sixth day, each time following their brushing with a one-minute rinse with one tablespoon of water. Patients were then told not to brush for a period of forty-eight hours but to rinse with water the evening of the sixth day, the following morning and evening (seventh day) and the morning of the eighth day. On the eighth day, patients were examined for dental plaque and gingivitis (Week 1). After completion of the examination, patients were instructed to brush twice daily for the next 5 days and once on the morning of the sixth day and then to immediately following their brushing with one-minute rinses with the unflavored mouthwash (described in Table 11). Patients were then told not to brush their teeth for the next forty-eight hours but were instructed to continue to rinse twice daily for one minute with one tablespoon of mouthwash. Patents were then examined for dental plaque and gingivitis (Week 2). During the course of the study, patients were not permitted to chew gum or to floss.

Clinical measurements were taken for both the plaque index and gingival index. Dental plaque was scored across the entire surface (distal buccal, central buccal and mesial buccal) of six teeth according to the following scheme:

0 = no dental plaque
1 = no plaque visible but there is evidence for plaque upon scraping
2 = plaque is visible to the eye
3 = gross obvious plaque The six teeth chosen were the Ramfjord teeth which include the maxillary right first molar, the maxillary left central incisor, the maxillary left first premolar, the mandibular left first molar, the mandibular right central incisor and the mandibular right first premolar. The amount of dental plaque on the teeth was also visualized with the use of disclosing tablets after which a series of intraoral photographs were taken of different areas of each patient's mouth.

Gingival index was scored according to the Loe and Silness Index (Journal of Periodontology 36:178, 1965) along the gingival margin of the six Ramfjord teeth using the following scheme:

0 = absence of inflammation
1 = mild inflammation, slight change in color and little change in texture; no bleeding upon probing
2 = moderate inflammation; there is moderate glazing, redness, edema and hypertrophy; bleeding upon probing
3 = severe inflammation; there is moderate redness and hypertrophy; tendency to spontaneous bleeding; ulceration Plaque and gingival index scores were totalled for the six teeth investigated. The data is presented in Table 11.

TABLE 11

Effect of Glycerin Lytic Mouthrinse on Reducing the Plaque Index and Gingival Index of Patients

| Patient | Plaque Index | | | Gingival Index | | |
|---|---|---|---|---|---|---|
| | Wk 0* | Wk 1** | Wk 2*** | Wk 0 | Wk 1 | Wk 2 |
| R. S. | 7 | 7 | 2(71)+ | 6 | 5 | 2(60) |
| J. W. | 8 | 9 | 3(67) | 7 | 8 | 5(38) |
| L. X. | 9 | 10 | 2(80) | 6 | 8 | 3(62) |
| Z. Y. | 13 | 13 | 5(72) | 8 | 8 | 6(25) |
| J. C. | 6 | 8 | 1(88) | 3 | 3 | 1(67) |
| J. P. | 8 | 8 | 4(50) | 7 | 8 | 3(62) |
| R. R. | 8 | 10 | 4(60) | 7 | 5 | 4(20) |

*Initial visit. No brushing for 48 hours, only twice rinsing with water.
**After one week on the water rinse.
***After one week on the lytic mouthrinse formulation listed in Example 10.
+Values in parenthesis in Week 2 indicate the percent reductions in the plaque index and gingival index when comparing Week 2 data with Week 1 data.

The foregoing example demonstrates that the dental rinse of the present invention was an effective agent in significantly reducing both dental plaque and gingival inflammation over the test period, when used in a regular home care regimen. A comparison of the Week 0 with Week 1 data indicates that we have established baseline values for these individuals on the control water rinse. A comparison of the data of the Week 1 water control to the Week 2 lytic mouthrinse indicates that all seven patients improved significantly in their oral hygiene (see Table 11). Intraoral photographs before and after lytic mouthrinse treatment confirmed the clinical measurements which demonstrated dramatic reductions in dental plaque (data not shown).

EXAMPLE 11

The following preferred dental mouthrinse was formulated in accordance with the present invention.

TABLE 12

Components of the preferred mint flavored dental mouthrinse formulation of Example 11, based on a total volume of 100 ml.

| Component | Concentration |
|---|---|
| Sorbitol | 30 gm |
| Tween 20 | 1.0 ml |
| Sodium Bicarbonate | 1.5 gm |
| Sodium Thiocyanate | 0.5 gm |
| Sodium Lauroyl Sarcosinate | 0.5 gm |
| Pluronic F127 | 0.012 gm |
| Alcohol | 7.0 ml |
| Redistilled Oil of Peppermint | 0.1 ml |
| Distilled Water q.s. | 100 ml |

There were six patients in this second clinical trial; however, in contrast to the first trial which was just two weeks, this clinical was extended for a longer period. As in the first trial, baseline data for water rinsing was obtained over the course of the first week which was followed by the lytic rinse formulation set out in Table 12. All instructions to patients were the same except that after the first three weeks of weekly clinical examinations, patients were seen every two weeks. For example, patients brushed and rinsed for the entire period of Week 4 and it was only the forty-eight hours prior to their appointments at the end of Week 5 that they stopped brushing but continued to rinse.

Measurements to determine the plaque index were the same as in the initial study; however, the determination of the gingival index was modified. Instead of just one gingival index value for the entire surface of each tooth, three values were obtained for the distal buccal, central buccal and mesial buccal surfaces. Values were then totalled. In addition to measurements of the plaque index and gingival index, a bleeding index was also done, as described by Polson and Caton, *Journal of Periodontology, Supplement*, 56, 1-3 (1985). In this technique, stimudents were repetively (four times) placed interproximally over a fifteen second period into themesial and distal sites of the six Ramfjord teeth. Stimudents were observed for the presence of blood. A positive was recorded as a value of one, while a negative was recorded as a zero. Values were totalled as for the plaque index and gingival index. At the completion of the study, an analysis was also made of the reduction, if any, of the bleeding on periodontal probing. Bleeding is scored as a 2 in the Loe and Silness Index and scores of 1 or 0 would indicate a reduction in the bleeding on probing. This latter technique is an often used screening method for testing the effectiveness of dentifrices on gingivitis (see Flemmig et al., *Journal of Dental Research, Abstracts*, 68, Abstract #1612, (1989).

Tables 13 thru 16 describe the data obtained using the sorbitol rinse of Table 12 in longer term studies.

The results given Table 13 indicate that all patients improved dramatically in reducing the amount of dental plaque on their teeth.

In comparison to a similarly conducted previous study using the commercial mouthrinse, Listerine, the mouthrinse of the present invention was significantly superior. At week 5, the average reduction in the plaque index of five patients on Listerine was 25% whereas in this study, the average reduction in six patients was 79%.

TABLE 13

Effect of a Sorbitol Lytic Mouthrinse on Reducing the Plaque Index of Patients

| Patient | Wt 1* | Wk 2** | Wk 3 | Wk 5 | Wk 7 |
|---|---|---|---|---|---|
| G. H. | 13 | 7.5(42)+ | 6(54) | 2.5(81) | 3(77) |
| N. S. | 11.5 | 4(65) | 2(83) | 2(83) | 1(92) |
| J. P. | 11.5 | 6.5(43) | 2(83) | 1.5(87) | 1.5(87) |
| L. X. | 12 | 6(50) | 3(75) | 1.5(88) | 0.5(96) |
| Z. Y. | 9 | 5(44) | 3(67) | 3.5(61) | 3(67) |
| R. R. | 10 | 6(40) | 4(60) | 2.5(75) | 1(90) |

*After one week on water rinse.
**Weeks 2 thru 7 indicate effects of lytic mouthrinse formulation listed in Table 12.
+Values in parentheses indicate the percent reductions in the plaque index compared to the Week 1 water rinse.

TABLE 14

Effect of Sorbitol Lytic Mouthrinse on Reducing the Gingival Index of Patients

| Patient | Wk 1* | Wk 2** | Wk 3 | Wk 5 | Wk 7 |
|---|---|---|---|---|---|
| G. H. | 22 | 13(41)+ | 15(32) | 13(41) | 10(55) |
| N. S. | 7 | 5(29) | 4(43) | 5(29) | 2(71) |
| J. P. | 16 | 14(13) | 11(31) | 11(31) | 8(50) |
| L. X. | 8 | 5(38) | 3(63) | 0(100) | 2(75) |
| Z. Y. | 19 | 14(26) | 16(16) | 21(0)≠ | 12(37) |
| R. R. | 22 | 14(36) | 7(68) | 8(64) | 7(68) |

*After one week on water rinse.
**Weeks 2 thru 7 indicate effects of lytic mouthrinse formulation listed in Table 12.
+Values in parentheses indicate the percent reductions in the gingival index compared to the Week 1 water rinse.
≠Increase in gingival index indicates increased inflammation.

TABLE 15

Effect of a Sorbitol Lytic Mouthrinse on Reducing the Bleeding Index of Patients

| Patient | Wk 1* | Wk 2** | Wk 3 | Wk 5 | Wk 7 |
|---|---|---|---|---|---|
| G. H. | 10 | 6(40)+ | 3(70) | 5(50) | 5(50) |
| N. S. | 0 | 0(0) | 0(0) | 0(0) | 0(0) |
| J. P. | 5 | 7(0)≠ | 5(0) | 4(20) | 1(80) |
| L. X. | 3 | 4(0)≠ | 0(100) | 0(100) | 0(100) |
| Z. Y. | 4 | 7(0)≠ | 6(0)≠ | 4(0) | 2(71) |
| R. R. | 9 | 6(33) | 3(67) | 2(78) | 4(55) |

*After one week on water rinse.
**Weeks 2 thru 7 indicate effects of lytic mouthrinse formulation listed in Table 12.
+Values in parentheses indicate the percent reduction in the bleeding index compared to the Week 1 water rinse.
≠Increase in bleeding index.

TABLE 16

Effect of a Sorbitol Lytic Mouthrinse on Bleeding on Probing

Number of Gingival Sites# with Bleeding on Probing

| Patient | Wk 1* | Wk 2** | Wk 3 | Wk 5 | Wk 7 |
|---|---|---|---|---|---|
| G. H. | 4 | 3(25)+ | 2(50) | 2(50) | 0(100) |
| N. S. | 0 | 0(0) | 0(0) | 0(0) | 0(0) |
| J. P. | 4 | 3(25) | 1(75) | 0(100) | 1(75) |
| L. X. | 0 | 0(0) | 0(0) | 0(0) | 1(0)≠ |
| Z. Y. | 4 | 0(100) | 2(50) | 3(25) | 1(75) |
| R. R. | 5 | 3(40) | 2(60) | 1(80) | 0(100) |

A total of eighteen sites are possible to yield bleeding on probing according to the design of the clinical testing.
*After one week on water rinse.
**Weeks 2 thru 7 indicate effects of lytic mouthrinse formulation listed in Table 12.
+Values in parentheses indicate the percent reductions in the bleeding on probing.
≠Increase in bleeding on probing indicates increased inflammation in specific gingival sites.

The results given in Table 14 indicate that the inflammatory status of all patients improved significantly with continued use of the lytic rinse.

In contrast to measurements for the plaque index and gingival index, the bleeding index thus far has had limited use in predicting the gingivitis status of patients. Nevertheless, it can be used as an indicator of the inflammatory status of patients. The results in Table 15 indicate that although initially there is some increase of the bleeding index in three of the patients, the bleeding index is reduced in these patients (in fact, in the five patients, bleeding is reduced by this technique) with continued use of the lytic rinse.

Compared to the Week 1 water rinse, five of the six patients, who showed bleeding or probing, had reductions in this parameter with continued use of the mouthrinse (see Table 16).

In addition to mouthrinses, the lytic formulation could easily be incorporated into different dentifrice preparations and other formulations described in Examples 12–18:

EXAMPLE 12

TABLE 17

Preferred Mint Flavored Mouthwash Formulation in accordance with the present invention

| Component | Concentration |
|---|---|
| Sorbitol | 80 gm |
| Sodium Bicarbonate | 2 gm |
| Sodium Thiocyanate | 2 gm |
| Sodium Lauroyl Sarcosinate | 1 gm |
| Alcohol | 15 ml |
| Tween 20 | 3 ml |
| Pluronic F127 | 0.012 gm |
| Oil of Peppermint | 0.1 ml |
| Water q.s. | 100 ml |

The formulation is utilized by rinsing the mouth for about 30 to 60 seconds from 1–3 times per day with about 15 ml of undiluted mouthwash.

EXAMPLE 13

TABLE 18

Preferred Mouthspray Formulation in accordance with the present invention

| Component | Concentration |
| --- | --- |
| Sorbitol | 40 gm |
| Sodium Bicarbonate | 1.5 gm |
| Sodium Thiocyanate | 0.5 gm |
| Sodium Lauroyl Sarcosinate | 0.5 gm |
| Tween 20 | 1 ml |
| Saccharin Sodium | 0.07 gm |
| Peppermint Spirit | 15 ml |
| Water q.s. | 100 ml |

The formulation is utilized by spraying aliquots of 0.25 to 0.50 ml onto each quadrant of the gingiva and tooth surface between 1 and 3 times per day.

EXAMPLE 14

TABLE 19

Preferred Toothpaste Gel Formulation in accordance with the present invention

| Component | Concentration |
| --- | --- |
| Glycerin | 40 gm |
| Sodium Bicarbonate | 2 gm |
| Sodium Thiocyanate | 1 gm |
| Sodium Lauroyl Sarcosinate | 1 gm |
| Tween 20 | 3 ml |
| Carboxymethyl Cellulose 120H | 1.8 gm |
| Saccharin Sodium (50% sol) | 0.2 ml |
| Oil of Peppermint | 0.6 ml |
| Mineral Oil | 2 ml |
| Silica | 21 gm |
| Water q.s. | 29 ml |

The formulation is utilized by cleaning the teeth with about 1 to 2 gm of paste between 1 to 3 times per day.

EXAMPLE 15

TABLE 20

Preferred Toothpaste Formulation in accordance with the present invention

| Component | Concentration |
| --- | --- |
| Sorbitol | 50 gm |
| Sodium Bicarbonate | 1 gm |
| Sodium Thiocyanate | 0.5 gm |
| Sodium Lauroyl Sarcosinate | 0.4 gm |
| Tween 20 | 3 ml |
| Methyl Paraben | 0.2 gm |
| Oil of Peppermint | 0.6 ml |
| Mineral Oil | 2 ml |
| Dicalcium Phosphate | 21 gm |
| Water q.s. | 21 ml |

The formulation is utilized by cleaning the teeth with about 1 to 2 gm of paste between 1 to 3 times per day.

EXAMPLE 16

TABLE 21

Preferred Chewing Gum in accordance with the present invention

| Component | Concentration |
| --- | --- |
| Sorbitol | 1400 mg |
| Corn Syrup | 165 mg |
| Sodium Bicarbonate | 10 mg |
| Sodium Thiocyanate | 10 mg |
| Sodium Lauroyl Sarcosinate | 10 mg |
| Tween 20 | 10 mg |

TABLE 21-continued

Preferred Chewing Gum in accordance with the present invention

| Component | Concentration |
| --- | --- |
| Paraffin Wax | 45 mg |
| Estergum | 140 mg |
| Coumarone Resin | 210 mg |
| Flavor q.s. | |

The formulation is utilized as needed.

EXAMPLE 18

TABLE 23

Preferred Candy (Lozenge) the present invention

| Component | Concentration |
| --- | --- |
| Acacia | as required for binding |
| Mannitol | 180 mg |
| Sorbitol | 600 mg |
| Sodium Bicarbonate | 1.5 mg |
| Sodium Thiocyanate | 0.5 mg |
| Tween 20 | 1 mg |
| Sodium Lauroyl Sarcosinate | 3 mg |
| Sodium Saccharin | 1.1 mg |
| Sodium Stearate | 5 mg |
| Licorice | 95 mg |
| Talc | 10 mg |
| Menthol | 1.0 mg |
| Lactose q.s. | 2000 mg |

The formulation is utilized as needed.

Thus, while there have been described what are presently contemplated preferred embodiments of the present invention, further changes and modifications could be made by those skilled in the art without departing from the scope of the invention, and it is contemplated to claim all such changes and modifications.

EXAMPLE 17

TABLE 22

Preferred Breath Freshener Tablet in accordance with the present invention

| Component | Concentration |
| --- | --- |
| Sorbitol | 300 mg |
| Sodium Bicarbonate | 2 mg |
| Sodium Thiocyanate | 2 mg |
| Sodium Lauroyl Sarcosinate | 2 mg |
| Tween 20 | 2 mg |
| Mannitol | 200 mg |
| Wintergreen Oil | 0.6 mg |
| Talc | 10 mg |
| Menthol | 0.8 mg |
| Oil of Peppermint | 0.3 mg |
| Sodium Stearate | 2 mg |
| Lactose q.s. | 1000 mg |

The formulation is utilized as needed.

EXAMPLE 18

TABLE 23

Preferred Candy (Lozenge) in accordance with the present invention

| Component | Concentration |
| --- | --- |
| Acacia | as required for binding |
| Mannitol | 180 mg |
| Sorbitol | 600 mg |
| Sodium Bicarbonate | 1.5 mg |
| Sodium Thiocyanate | 0.5 mg |
| Tween 20 | 1 mg |
| Sodium Lauryl Sarcosinate | 3 mg |
| Sodium Saccharin | 1.1 mg |
| Sodium Stearate | 5 mg |

TABLE 23-continued

Preferred Candy (Lozenge) in accordance with the present invention

| Component | Concentration |
| --- | --- |
| Licorice | 95 mg |
| Talc | 10 mg |
| Menthol | 1.8 mg |
| Lactose q.s. | 2000 mg |

The formulation is utilized as needed.

Thus, while there have been described what are presently contemplated preferred embodiments of the present invention, further changes and modifications could be made by those skilled in the art without departing from the scope of the invention, and it is contemplated to claim all such changes and modifications.

I claim:

1. An oral rinse formulation comprising humectant in a concentration from approximately 20% to about 80%, bicarbonate ion from about 0.5% to about 2%, anionic surfactant detergent in a concentration of 0.05% to about 1% and non-ionic surfactant detergent in a concentration from about 0.01% to about 3%.

2. The oral rinse formulation recited in claim 1 wherein said humectant comprises glycerol in a concentration from approximately 30% to approximately 50%, said bicarbonate ion comprises sodium bicarbonate from about 0.5% to about 2%; said anionic surfactant detergent is selected from the group consisting of sodium lauroyl sarcosinate and sodium lauroyl sulfate, said non-ionic surfactant detergent is selected from the group consisting of Tween 20, polymers of polyoxyethylene, polymer of polypropylene and structurally similar compounds, and further comprising inorganic monovalent anions, selected from the group consisting of thiocyanate, chloride and fluoride ions in a concentration from about 0.5% to about 2%.

3. The oral rinse formulation recited in claim 2 wherein said inorganic monovalent anion comprise sodium thiocyanate; said ionic surfactant detergent comprises sodium lauroyl sarcosinate; said non-ionic surfactant detergent comprises Tween 20.

4. The oral rinse formulation recited in claim 3 wherein said humectant comprises sorbitol in a concentration from about 20% to about 50%.

5. The oral rinse formulation recited in claim 2 wherein said humectant is glycerol in a concentration of about 40%.

6. The oral rinse formulation recited in claim 4 wherein said humectant is sorbitol in a concentration of about 30%.

7. The oral rinse formulation recited in claim 1 wherein said mouthrinse further comprises sweetening, coloring, and/or flavoring agents.

8. The formulation recited in claim 2 which is suitably formulated into the group selected from an oral rinse, a mouth spray, a toothpaste gel composition, a toothpaste, a chewing gum, a breath freshener tablet, a candy and a lozenge.

9. An antibacterial formulation comprising: humectant in a concentration of from about 20% to about 80%; bicarbonate ion from about 0.5% to about 2%; anionic surfactant detergent in a concentration of 0.05% to about 1%, non-ionic surfactant detergent in a concentration from about 0.01% to about 3%, and a makeup quantity of water.

10. An oral rinse formulation comprising glycerol in a concentration from approximately 20% to approximately 80%; sodium bicarbonate from about 0.5% to about 2%, anionic surfactant detergent selected from the group consisting sodium lauroyl sarcosinate and sodium lauroyl sulfate; non-ionic surfactant detergent selected from the group consisting of Tween 20, Polymers of Polyoxyethylene and polymers of polypropylene; and, inorganic monovalent anions selected from the group consisting of thiocyanate, chloride and fluoride ions in a concentration from about 0.5% to about 2%.

11. An oral rinse formulation comprising sorbitol in a concentration from approximately 20% to approximately 80%; sodium bicarbonate from about 0.5% to about 2%, anionic surfactant detergent selected from the group consisting sodium lauroyl sarcosinate and sodium lauroyl sulfate; non-ionic surfactant detergent selected from the group consisting of Tween 20, Polymers of Polyoxyethylene and polymers of polypropylene; and, inorganic monovalent anions selected from the group consisting of thiocyanate, chloride and fluoride ions in a concentration from about 0.5% to about 2%.

12. A method for treating and inhibiting dental caries, plaque, gingivitis, malodor or periodontopathic conditions in mammals, comprising: introducing the formation recited in claim 1, 2, 8, 9, 10, or 11 into the oral cavity of the mammal by a carrier or dispenser.

* * * * *